United States Patent
Bouckenooghe et al.

(10) Patent No.: US 10,143,741 B2
(45) Date of Patent: *Dec. 4, 2018

(54) IMMUNIZATION COMPOSITIONS AND METHODS

(71) Applicant: Sanofi Pasteur SA, Lyons (FR)

(72) Inventors: Alain Bouckenooghe, Singapore (SG); Remi Forrat, Serezin du Rhone (FR); Denis Crevat, Beynost (FR)

(73) Assignee: Sanofi Pasteur SA, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,970

(22) Filed: Apr. 14, 2014

(65) Prior Publication Data
US 2014/0220073 A1 Aug. 7, 2014

Related U.S. Application Data

(63) Continuation of application No. 13/019,243, filed on Feb. 1, 2011, now Pat. No. 8,697,353.

(30) Foreign Application Priority Data

Feb. 4, 2010 (EP) .................................. 10305114

(51) Int. Cl.
| | |
|---|---|
| *A61K 39/00* | (2006.01) |
| *A61K 39/12* | (2006.01) |
| *A61K 39/39* | (2006.01) |
| *A61K 39/395* | (2006.01) |
| *A61K 47/00* | (2006.01) |
| *A61K 39/295* | (2006.01) |
| *A61K 39/05* | (2006.01) |
| *A61K 39/08* | (2006.01) |
| *A61K 39/02* | (2006.01) |
| *A61K 39/102* | (2006.01) |
| *C12N 7/00* | (2006.01) |

(52) U.S. Cl.
CPC ........ *A61K 39/295* (2013.01); *A61K 39/0015* (2013.01); *A61K 39/0018* (2013.01); *A61K 39/05* (2013.01); *A61K 39/08* (2013.01); *A61K 39/099* (2013.01); *A61K 39/102* (2013.01); *A61K 39/12* (2013.01); *A61K 2039/522* (2013.01); *A61K 2039/525* (2013.01); *A61K 2039/545* (2013.01); *A61K 2039/55505* (2013.01); *A61K 2039/70* (2013.01); *C12N 7/00* (2013.01); *C12N 2760/18434* (2013.01); *C12N 2760/18734* (2013.01); *C12N 2760/20234* (2013.01); *C12N 2770/24134* (2013.01); *C12N 2770/32634* (2013.01); *C12N 2770/36234* (2013.01); *Y02A 50/386* (2018.01); *Y02A 50/388* (2018.01)

(58) Field of Classification Search
CPC .. A61K 2300/00; A61K 39/092; A61K 39/00; A61K 39/12; C07K 14/315

USPC ............................................................ 435/5
See application file for complete search history.

(56) References Cited

U.S. PATENT DOCUMENTS

| 8,025,887 B2 | 9/2011 | Kinney et al. | |
| 2008/0085288 A1* | 4/2008 | Guy et al. ................. | 424/218.1 |
| 2010/0239612 A1* | 9/2010 | Guy et al. ................. | 424/218.1 |

FOREIGN PATENT DOCUMENTS

| WO | WO-03/101397 A2 | 12/2003 |
| WO | WO-08/065315 A1 | 6/2008 |

OTHER PUBLICATIONS

Ada, Gordon, Review: Overview of Vaccines and Vaccination, 2005, Molecular Biotechnology, 29:255-271.*
WHO, UNICEF, World Bank. State of the world's vaccines and immunization, 3rd ed. Geneva, World Health Organization,2009:130-145.*
Ada, "Overview of vaccines and vaccination," Molec Biotechnol. 29:255-71 (2005).
Brandler et al., "Pediatric measles vaccine expressing a dengue antigen induces durable serotype-specific neutralizing antibodies to dengue virus," PLoS Negl Trop Dis. 1(3):1-12 (2007).
Chokephaibulkit, "Combination vaccines," J Med Assoc Thai. 85(Suppl 2):S694-9 (2002).
King et al., "Simultaneous administration of childhood vaccines: an important public health policy that is safe and efficacious," Pediatr Infect Dis J. 13(5):394-407 (1994).
Sabchareon et al., "Protective efficacy of the recombinant, live-attenuated, CYD tetravalent dengue vaccine in Thai schoolchildren: a randomised, controlled phase 2b trial," The Lancet, Published online, Sep. 11, 2012.
Tangy et al., "Live attenuated measles vaccine as a potential multivalent pediatric vaccination vector," Viral Immunol. 18(2):317-26 (2005).
WHO, UNICEF, World Bank. State of the world's vaccines and immunization, 3rd ed. Geneva, World Health Organization, 2009.
Nascimento Silva et al., "Mutual interference on the immune response to yellow fever vaccine and a combined vaccine against measles, mumps and rubella," Vaccine. 29(37):6327-34 (2011).
Kroger et al., "General Recommendation for Vaccination & Immunoprophylaxis," excerpt from 2016 Yellow Book, Chapter 2: The Pre-Travel Consulation, Centers for Disease, Control, and Prevention (2016) (2 pages).
del Angel et al., "Dengue vaccines: strongly sought by not a reality just yet," PLoS Pathogens. 9(10):e1003551 (4 pages) (2013).
Capeding et al., "Clinical efficacy and safety of a novel tetravalent dengue vaccine in healthy children in Asia: a phase 3, randomised, observer-masked, placebo-controlled trial," Lancet. 384(9951):1358-65 (2014).
Dorigatti, "Refining the characterisation of the Sanofi Pasteur dengue vaccine's efficacy profile using machine learning," 49th Scientific Meeting of the Societa Italiana di Statistica, Jun. 20, 2018. Palermo, Italy. (15 pages).

(Continued)

*Primary Examiner* — Barry A Chestnut
(74) *Attorney, Agent, or Firm* — Clark & Elbing LLP; Susan M. Michaud

(57) ABSTRACT

The present invention provides methods and compositions to induce neutralizing antibodies in mammals to serotypes of dengue virus, measles virus, mumps virus, rubella and/or VZV virus.

7 Claims, No Drawings

(56) References Cited

OTHER PUBLICATIONS

Hadinegoro et al., "Efficacy and long-term safety of a dengue vaccine in regions of endemic disease," N Engl J Med. 373(13):1195-206 (2015).
Moodie et al., "Neutralizing antibody correlates analysis of tetravalent dengue vaccine efficacy trials in Asia and Latin America," J Infect Dis. 217(5):742-53 (2018).
Rabaa et al., "Genetic epidemiology of dengue viruses in phase III trials of the CYD tetravalent dengue vaccine and implications for efficacy," Elife. 6. pii:e24196 (2017) (22 pages).
Sridhar et al., "Effect of dengue serostatus on dengue vaccine safety and efficacy," N Engl J Med. DOI: 10.1056/NEJMoa1800820 (2018) (14 pages).
Villar et al., "Efficacy of a tetravalent dengue vaccine in children in Latin America," N Engl J Med. 372(2):113-23 (2015).

\* cited by examiner

IMMUNIZATION COMPOSITIONS AND METHODS

BACKGROUND OF THE INVENTION

Dengue is the second most important infectious tropical disease after malaria with approximately one-half of the world's population living in areas where there is a risk of epidemic transmission. There are estimated to be 50-100 million cases of dengue fever every year resulting in 500,000 patients being hospitalized for hemorrhagic dengue fever and resulting in approximately 25,000 deaths. Dengue fever virus infections are endemic in more than 100 tropical countries and hemorrhagic dengue fever has been documented in 60 of these countries (Gubler, 2002, TRENDS in Microbiology, 10: 100-103; Monath, 1994, Proc. Natl. Acad. Sci., 91: 2395-2400).

Dengue fevers are caused by four viruses of the flavivirus genus which are of similar serological type but differ antigenically (Gübler et al., 1988, in: Epidemiology of arthropod-borne viral disease. Monath TPM, editor, Boca Raton (Fla.): CRC Press: 223-60; Kautner et al., 1997, J. of Pediatrics, 131: 516-524; Rigau-Pérez et al., 1998, Lancet, 352: 971-977; Vaughn et al., 1997, J. Infect. Dis., 176: 322-30). "Dengue fever viruses" or "dengue viruses" are positive single-strand RNA viruses belonging to the *Flavivirus* genus of the family of flaviviridae. The genome in RNA comprises a 5' type I end but lacks a 3' poly-A tail. The organization of the genome comprises the following elements: a 5' non-coding region (NCR), a region encoding structural proteins (capsid (C), pre-membrane/membrane (prM/M), envelope (E)) and a region encoding non-structural proteins (NS1-NS2A-NS2B-NS3-NS4A-NS4B-NS5) and a 3' NCR. The viral genomic RNA is associated with the capsid proteins to form a nucleocapsid. Typical of flaviviruses, the dengue viral genome encodes an uninterrupted coding region which is translated into a single polyprotein which is post-translationally processed.

Dengue viruses are maintained within a cycle involving mammals and the *Aedes* mosquito. Infection in a mammal is initiated by injection of the dengue virus during the blood meal of an infected *Aedes* mosquito whereby the dengue virus is primarily deposited in the extravascular tissues. The incubation period of the virus after a mosquito bite is approximately 4 days (from 3 to 14 days).

The first category of mammalian cells to be infected after inoculation of the mammalian subject are the dendritic cells, which then migrate to the lymphatic ganglia (Wu et al., 2000, Nature Med., 7: 816-820). In addition to dendritic cells, monocytes and macrophages are among the first targets of dengue virus. After initial replication in the skin and lymphatic ganglia, the dengue virus appears in the blood in the course of the acute febrile stage, generally for 3 to 5 days.

Infection with one serotype of dengue may produce a spectrum of clinical disease from non-specific viral syndrome to severe fatal hemorrhagic disease. Routine laboratory diagnosis of dengue fever is based on isolation of the virus and/or the detection of antibodies specific to dengue fever virus. Primary infection may be asymptomatic or may result in dengue fever. Dengue fever is characterized by a two-phase fever, headaches, pains in various parts of the body, prostration, eruptions and lymphadenopathy (Kautner et al., 1997, J. of Pediatrics, 131: 516-524; Rigau-Pérez et al., 1998, Lancet, 352: 971-977). The viremic period is of the same length as the febrile period (Vaughn et al., 1997, J. Infect. Dis., 176: 322-30). Cure of dengue fever is complete after 7 to 10 days, but prolonged asthenia is normal. Reduced leukocyte and platelet numbers frequently occur.

Dengue haemorrhagic fever (DHF) is a potentially deadly complication of dengue virus infection. DHF is characterized by a high fever and symptoms of dengue fever, but with extreme lethargy and drowsiness. Increased vascular permeability and abnormal homeostasis can lead to a decrease in blood volume, hypotension, and in severe cases, hypovolemic shock and internal bleeding. Two factors appear to play a major role in the occurrence of hemorrhagic dengue fever—rapid viral replication with a high level of viremia (the severity of the disease being associated with the level of viremia; Vaughn et al., 2000, J. Inf. Dis., 181: 2-9) and a major inflammatory response with the release of high levels of inflammatory mediators (Rothman and Ennis, 1999, Virology, 257: 1-6). The mortality rate for hemorrhagic dengue fever can reach 10% without treatment, but is ≤1% in most centers with experience of treatment (WHO Technical Guide, 1986. Dengue hemorrhagic fever: diagnosis, treatment and control, p. 1-2. World Health Organization, Geneva, Switzerland).

Dengue shock syndrome (DSS) is usually a progression of DHF and is frequently fatal. DSS results from generalized vasculitis leading to plasma leakage into the extravascular space. DSS is characterized by rapid and poor volume pulse, hypotension, cold extremities, and restlessness.

The four serotypes of dengue virus possess approximately 60-80% sequence homology. Infection with one dengue serotype provides durable homologous immunity but limited heterologous immunity. (Sabin, 1952, Am. J. Trop. Med. Hyg., 1: 30-50). Consequently, an individual may subsequently become infected with a different serotype. A second infection arising from a different serotype of dengue fever is, in theory, a risk factor for the development DHF. The majority of patients that exhibit DHF have been previously exposed to at least one of the four serotypes of dengue viruses. However, DHF is multifactorial—factors include the strain of virus involved and the age, immune status and genetic predisposition of the patient. It is thought that upon homologous re-infection, antibodies specific to the serotype bind to the surface proteins and prevent the virus from binding to target cells. However, upon re-infection by a heterologous dengue serotype, the heterologous virus will activate the immune system to attack as if it was the first serotype. These antibodies to the prior serotype bind to but do not inactivate the virus. The immune response attracts numerous macrophages which the heterologous serotype then infects. It is hypothesized that the antibodies generated by a previous dengue serotype infection can result in symptoms of enhanced severity when the individual is subsequently infected by a different dengue serotype. Consequently, it is desirable to immunize an individual against all four serotypes of dengue.

There is no specific treatment against dengue fever. Treatment for dengue fever is symptomatic, with bed rest, control of the fever and pain through antipyretics and analgesics, and adequate drinking. The treatment of hemorrhagic dengue fever requires balancing of liquid losses, replacement of coagulation factors and the infusion of heparin.

One population particularly susceptible to the effects of dengue virus infection are children. The effects of dengue virus infection are more severe in children. Although, the availability of multiple pediatric vaccines has alleviated the threat of multiple diseases to the pediatric population, the recommended administration of these vaccines has created an increasingly complex and crowded schedule of vaccinations. Current protocols for the administration of dengue vaccines anticipate the need for multiple vaccinations to ensure complete protection against all serotypes. The addition of such a dengue vaccination schedule to the already crowded childhood vaccination schedule raises issues of compliance with the recommended pediatric vaccination schedule, particularly in those areas of the world where regular availability of healthcare is difficult to obtain. Unfortunately, these same areas are where the threat of dengue fever is particularly acute. Consequently, there is a desire to combine multiple vaccines by co-administration to enhance compliance with the recommended vaccination schedule.

There has been some success in minimizing the frequency of vaccination by combining multiple vaccinations into a single dosage form. However, there is the potential for incompatibility among the different agents in a single dosage form. Additionally, the administration of multiple vaccines at a single time also creates issues for effective vaccination. Whenever a multivalent vaccine is administered (or multiple vaccines are co-administered) in combination, each individual antigen of the combination induces an immunological response. It is possible to inhibit the immune system's ability to adequately respond to all of the antigens administered and not provide a durable protective response to one or more of the antigens.

The present invention addresses the foregoing needs by providing methods and compositions to enable concomitant mumps, measles and rubella vaccination with dengue vaccination against dengue serotypes 1, 2, 3, and 4.

DETAILED DESCRIPTION OF THE INVENTION

In one embodiment, the invention provides a method of inducing neutralizing antibodies against four serotypes of dengue virus and measles virus in a mammal, comprising the administration of dengue vaccinal composition and the co-administration of a measles vaccinal composition to said mammal.

In one embodiment, the invention provides a method of inducing neutralizing antibodies against four serotypes of dengue virus, mumps virus, measles virus and rubella in a mammal, comprising the administration of dengue vaccinal composition and the co-administration of an MMR vaccinal composition to said mammal.

In one embodiment, the invention provides a method of inducing neutralizing antibodies against four serotypes of dengue fever, mumps virus, measles virus, rubella, and VZV in a mammal, comprising the administration of dengue vaccinal composition and the co-administration of an MMRV vaccinal composition to said mammal.

In one embodiment, the invention provides a method of inducing neutralizing antibodies against four serotypes of dengue virus, mumps virus, measles virus and rubella as well as diphtheria, tetanus, pertussis, poliomyelitis and Hib antigens in a mammal, comprising the administration of vaccinal dengue viruses of four serotypes of dengue and the co-administration of an MMR vaccinal composition followed by an administration of a composition comprising diphtheria, tetanus, pertussis, poliomyelitis and Hib antigens to said mammal.

In one embodiment of the invention, the administration of vaccinal dengue viruses of four serotypes of dengue is achieved by the administration of a tetravalent vaccinal virus composition.

In one embodiment of the invention, the administration of vaccinal dengue viruses of four serotypes of dengue is achieved by the co-administration of two bivalent vaccinal dengue virus compositions.

In one embodiment of the invention, the administration of vaccinal dengue viruses of four serotypes of dengue is achieved by the administration of a tetravalent vaccinal virus composition comprising CHIMERIVAX™ (CYD) DEN-1, 2, 3 and 4.

In one embodiment of the invention, the administration of vaccinal dengue viruses of four serotypes of dengue is achieved by the administration of a tetravalent vaccinal virus composition wherein the quantity of vaccinal viruses of dengue fever of serotypes 1, 2, 3 and 4 lies within a range from $10^3$ to $10^6$ $CCID_{50}$.

Monovalent; Bivalent, Etc.

A dose, composition or vaccine is termed "monovalent" when in addition to a pharmaceutically acceptable excipient, it contains an antigen(s) derived from a single strain of microorganism designed to elicit a neutralizing antibody response against a particular pathogen and multivalent when it contains antigens from multiple strains designed to elicit neutralizing antibodies against multiple pathogens. The nomenclature used is consistent with conventional nomenclature. For example, a dose, composition or vaccine is considered bivalent, trivalent or tetravalent when it contains antigens designed to elicit neutralizing antibodies against two, three or four pathogens respectively. Multivalent compositions may be prepared by simple mixing of monovalent compositions. Such multivalent compositions may be prepared in advance at the point of manufacture or may be combined by the end user at the time of administration to the subject. The administration of vaccinal viruses of four serotypes of dengue virus may be achieved by the administration or co-administration of monovalent or bivalent vaccinal dengue viruses or by the administration of a tetravalent vaccinal dengue virus composition. As used herein, a "tetravalent dengue composition" comprises antigens which induce neutralizing antibodies against all four serotypes of dengue.

Vaccinal Dengue Composition

The term "vaccinal dengue composition" refers to a composition comprising vaccinal dengue virus(es) and/or dengue immunoprotein(s). The vaccinal dengue composition may comprise one or more vaccinal dengue viruses, one or more dengue immunoproteins or a combination of one or more vaccinal dengue viruses and one or more dengue immunoproteins.

Vaccinal Dengue Virus

In the context of the present invention, "vaccinal dengue virus" is refers to a dengue virus which is capable of inducing neutralizing antibodies against one or more serotypes of dengue virus by the administration of such vaccinal dengue virus to an immunocompetent mammal. Examples of vaccinal dengue virus(es) include inactivated dengue virus(es), attenuated dengue virus(es), and chimeric dengue virus(es). Serotypes of dengue virus include serotypes 1, 2, 3, and 4.

Inactivated Dengue Virus

A virus is regarded as being "inactivated" if it is incapable of replication to any significant degree in cells permissive for replication of the wild type virus. Viruses may be inactivated by a number of means well known to those in the art, including but not limited to serial passaging, genetic manipulation, chemical treatments, or radiation (including heat or electromagnetic radiation typically in the forms of X-ray or ultraviolet radiation). Inactivated dengue viruses are described in U.S. Pat. No. 6,254,873 issued Jul. 3, 2001.

Attenuated Dengue Virus

An "attenuated virus" is a virus which replicates in a permissive host cell but the replicative efficiency of which is significantly reduced relative to the wild-type virus in the same cell type. Attenuated viruses can replicate to some minor extent, degree, it does not induce a disease state associated with the wild-type virus in a mammal. Examples of attenuated viruses are known in the art. An attenuated virus may be prepared, for example, from a wild-type virus by recombinant DNA technology, site directed mutagenesis, genetic manipulation, serial passage, chemical treatment, chemical mutagenesis or electromagnetic radiation. An attenuated virus useful in the present invention may generate side effects of moderate intensity (i.e. medium to slight, or none) in the majority of vaccinated individuals, while retaining its ability to induce a neutralizing antibodies in a mammal.

Although attenuated viruses replicate to a lesser degree than wild-type viruses in typical host cells, such attenuated viruses may be produced efficiently in cells which are able to complement functions disrupted in the attenuated virus ("producer cells"). Producer cells may be naturally occurring variants of permissive host cells or may be generated by other means such recombinant DNA technology. In preparing engineered producer cells using recombinant DNA technology, the cell is modified by the insertion of exogenous nucleic acids which complement the functions which are disrupted in the attenuated virus. Such exogenous nucleic acids may be incorporated into the genome of the cell or may be maintained extrachromosomally.

A vaccinal dengue virus used in the context of the practice of the present invention may be an attenuated dengue virus. An attenuated dengue virus may be derived from dengue virus serotype 1, 2, 3, or 4. In one embodiment, the attenuated dengue virus is an attenuated dengue virus that possesses a replicative efficiency in a permissive cell type is at least one order of magnitude less than the wild type virus in the same cell type. In other embodiments, the attenuated dengue virus is attenuated for replication to a degree at least two orders of magnitude, three orders of magnitude, four orders of magnitude, five orders of magnitude, six orders of magnitude, seven orders of magnitude or more relative to the wild type virus in the same cell type.

In one embodiment, the vaccinal dengue virus is an attenuated dengue virus the growth of which at 37° C. or 39° C. in Huh-7, VERO and/or C6/36 liver cells results in a maximum titer which is at least 10 times less than maximum titer obtained with the wild parent strain under the same culture conditions and as measured using a given method for determining titer. Examples of attenuated vaccinal dengue viruses useful in the practice of the present invention include the VDV-1, VDV-2, and the strains described for example in applications WO02/66621, WO0057904, WO0057908, WO0057909, WO0057910, WO02/0950075 and WO02/102828.

"VDV" or "Vero dengue vaccine" designates an attenuated dengue virus capable of replication in Vero cells and capable of inducing a specific humoral response, including the induction of neutralizing antibodies, in a mammal. "VDV-1" is a virus derived from the wild-type DEN-1 16007 strain which has undergone 11 passages through PDK cells (DEN-1 16007/PDK11) and which has subsequently been amplified in Vero cells at 32° C., the RNA of which has been purified and transfected in Vero cells. The VDV-1 strain has 14 additional mutations in comparison with the DEN-1 16007/PDK13 vaccinal strain (13 passes through PDK—Primary Dog Kidney—cells). The DEN-1 16007/PDK13 strain, also called "LAV1", has been described in patent application EP1159968 in the name of Mahidol University and has been filed with the National Microorganisms Cultures Collection (CNCM) under number I-2480. A process for preparing and characterizing the VDV-1 strain has been described in the international patent application filed under number PCT/IB 2006/001313 in the names of Sanofi-Pasteur and the Center for Disease Control and Prevention.

"VDV-2" is a strain which has been obtained from wild strain DEN-2 16681 which has undergone 50 passes through PDK cells (DEN-2 16681/PDK50), plate purified, the RNA from which has been extracted and purified before being transfected in Vero cells. The VDV-2 strain has subsequently been obtained by plate purification and amplification in Vero cells. The VDV-2 strain has 10 additional mutations in comparison with the DEN-2 16681/PDK53 vaccinal strain (53 passes through PDK cells), including 4 silent mutations. The DEN-2 16681/PDK53 strain, also known as "LAV2", has been described in patent application EP1159968 in the name of Mahidol University and has been filed with the National Microorganisms Cultures Collection (CNCM) under number I-2481. A process for preparing and characterizing the VDV-2 strain has been described in the international patent application filed under number PCT/IB 2006/001513 in the names of Sanofi-Pasteur and the Center for Disease Control and Prevention.

The VDV 1 and 2 strains are prepared by amplification in Vero cells. The viruses produced are harvested and clarified from cell debris by filtration. The DNA is digested by treatment with enzymes. Impurities are eliminated by ultrafiltration. Infectious titers may be increased by a concentration method. After adding a stabilizer, the strains are stored in lyophilized or frozen form before use and then reconstituted when needed.

Chimeric Dengue Virus

A vaccinal dengue virus of the present invention may also be a chimeric dengue virus. A chimeric dengue virus is a non-dengue virus the genome of which has been modified to encode envelope proteins of a dengue virus such that infection of a cell by a chimeric dengue virus results in the expression of envelope protein(s) of dengue virus in an infected cell. The non-dengue virus used for the preparation of chimeric dengue viruses may be derived from wild-type or inactivated non-dengue viruses. Examples of non-dengue viruses useful for the transfer and expression of exogenous nucleic acids in mammalian cells and useful in the preparation of dengue chimeric viruses are well known in the art. Illustrative examples of non-dengue viruses which may be employed in the construction of chimeric dengue viruses include flaviviruses, poxviruses, adenoviruses, and adeno-associated viruses. In one embodiment of the invention, the non-dengue virus is a wild-type or attenuated flavivirus. In one embodiment of the invention, the non-dengue virus is an attenuated yellow fever virus wherein the viral genome of such attenuated fever virus has been modified to encode the prM and E genes of a dengue virus serotype. Chimeric dengue viruses cause the expression of dengue envelope proteins in an infected cell inducing an immune response comprising antibodies neutralizing the dengue serotype from which the dengue envelope protein originates may therefore be used in the context of this invention. Examples of chimeric viruses useful in the practice of the present invention include the dengue dengue/YF chimeric viruses described in patent application WO 98/37911 and dengue/ dengue fever chimeras such as those described in patent applications WO9640933 and WO0160847.

In one embodiment, the chimeric YF/dengue virus comprises the genomic backbone of the attenuated yellow fever virus strain YF17D (Theiler M. and Smith H. H. (1937) J. Exp. Med., 65, p.767-786) (viruses YF17D/DEN-1, YF17D/DEN-2, YF17D/DEN-3, YF17D/DEN-4). Examples of YF17D strains which may be used include YF17D204 (YF-Vax®, Sanofi-Pasteur, Swifwater, Pa., USA; Stamaril®, Sanofi-Pasteur, Marcy l'Etoile, France; ARILVAX™, Chiron, Speke, Liverpool, UK; FLAVIMUN®, Berna Biotech, Bern, Switzerland; YF17D-204 France (X15067, X15062); YF17D-204,234 US (Rice et al., 1985, Science, 229: 726-733), or again the related strains YF17DD (Genbank access number U17066), YF17D-213 (Genbank access number U17067) and the strains YF17DD described by Galler et al. (1998, Vaccines, 16(9/10): 1024-1028). Any other attenuated yellow fever virus strain which may be used in man may be used to construct chimeras in the context of this invention.

One example of a chimeric dengue virus suitable for use in the practice of the present invention is the "CHIMERIVAX™ dengue" or "CYD", a chimeric yellow fever (YF) virus which comprises the genomic skeleton of a YF virus in which the sequences coding for the pre-membrane (prM) and envelope (E) proteins have been replaced by nucleic acid sequences encoding the corresponding structural proteins of a dengue virus. Construction of chimeric CHIMERIVAX™ (CYD) virus may be achieved in substantial accordance with the teaching of Chambers, et al. (1999) J Virology 73(4):3095-3101. A chimeric dengue virus containing the prM and E sequences of a serotype 1 dengue fever strain (DEN-1) is referred to as "CYD-1 or CYD DEN1". A chimeric YF containing the prM and E sequences of a DEN-2 strain is referred as "CYD-2 or CYD DEN2". A chimeric YF virus containing the prM and E sequences of a DEN-3 strain is referred to as "CYD-3 or CYD DEN3". A chimeric dengue virus containing the prM and E sequences of a DEN-4 strain is referred to as "CYD-4 or CYD DEN4". The preparation of these dengue CHIMERIVAX™ (CYD) viruses have been described in detail in international patent applications WO 98/37911 and WO 03/101397, to which reference may be made for a precise description of the processes for their preparation. The chimeras described in the examples have been generated by using prM and E sequences from strains DEN 1 PUO359 (TYP1140), DEN2 PUO218, DEN3 PaH881/88 and DEN 4 1228 (TVP 980). Alternatively, other dengue fever virus strains may be used as a source of nucleic acids to facilitate construction of chimeric viruses useful in the practice of the present invention.

An example of a vaccinal dengue virus of serotype 1 dengue virus may for example be the vaccinal strain VDV1 or a CHIMERIVAX™ (CYD) DEN-1, a YF17D/DEN-1 chimeric virus comprising prM and E genes of the DEN-1 16007/PDK13 strain. An example of a vaccinal virus of serotype 2 dengue virus is the vaccinal strain VDV2 or a CHIMERIVAX™ (CYD) DEN-2, a YF17D/DEN-2 chimeric virus comprising prM and E genes of the DEN-2 16681/PDK53 strain. An example of a vaccinal virus of serotype 3 dengue virus is CHIMERIVAX™ (CYD) DEN-3, a YF17D/DEN-3 chimeric virus. An example of a vaccinal virus of serotype 4 dengue virus is CHIMERIVAX™ (CYD) DEN-4, a YF17D/DEN-4 chimeric virus. The skilled artisan may refer to the aforementioned published international patent applications for a detailed description of the strains mentioned, the processes for obtaining them and the construction of these chimeric viruses.

Dengue Immunoproteins

The dengue vaccinal composition may also comprise dengue immunoproteins. Dengue immunoproteins are dengue structural proteins or derivatives thereof that when administered to an immunocompetent mammal induce serum neutralizing antibodies against dengue serotypes 1, 2, 3, and/or 4. Dengue immunoproteins include native, derivatized or denatured forms of dengue structural proteins including chemical conjugates, immunological fragments, and fusion proteins thereof.

The genomic sequence and organization of the dengue viral genome is well characterized in the art facilitating the recombinant production of such proteins. See, e.g., Sughrue, et al. (1997) J. General Virology 78(8): 1861-1866. Dengue virus particles are composed of three structural proteins: a genome associated capsid protein, a membrane associated protein (M) that is derived during virus maturation by internal cleavage from a glycosylated precursor protein (prM) and a membrane anchored hemagglutinating envelope protein (E). It is believed that E is the major antigenic determinant for serotype specificity. Markoff, J. (1989) J Virol. 63(8):3345-3352. However, the product of the prM gene, the glycosylated M protein and fragments thereof also possesses antigenic capacity capable of eliciting a specific immune response. Vasquez, et al. (2002) Vaccine 20:1823-1830. The recombinant expression of dengue envelope proteins is well known in the art. See, e.g. Zhao, et al (1987) J Virol. 61:4019-4022. Alternatively dengue structural proteins may be isolated from dengue viral particles or cells infected by dengue virus.

Dengue structural proteins may be administered to a mammal to elicit a specific immune response to induce serum neutralizing antibodies against the four serotypes of dengue. Such structural proteins may be administered in native, derivatized or denatured form. Denaturation of dengue structural proteins may be achieved using conventional denaturing methods such as heat or chemical denaturant chemicals such as formaldehyde or beta-propionolactone. Alternatively, subunits of such dengue surface proteins may be used to elicit an immune response against one or more serotypes of dengue. Immunologically active epitopes of the dengue structural proteins are described in the literature. The dengue vaccinal compositions of the present invention include monovalent subunit vaccines against a serotype of dengue and include multivalent dengue subunit vaccines capable of eliciting immune responses against multiple dengue serotypes.

Such dengue structural proteins, derivatives and subunits thereof may also be conjugated to carrier molecules to provide conjugate dengue antigens useful in generating neutralizing antibodies in an immunocompetent mammal and useful in the practice of the present invention. Such conjugation may be achieved by chemical conjugation techniques or through the recombinant expression of fusion proteins comprising the dengue structural proteins or immunologically active subunits thereof and the carrier protein. Examples of carrier molecules which may be used in the preparation of conjugates useful in the practice of the present invention include diphtheria toxoid, tetanus toxoid, fragment C of tetanus toxin, mutants of diphtheria toxin including CRM197, CRM176, CRM228, CRM 45, CRM 9, CRM 45, CRM102, CRM 103 and CRM107, pneumococcal pneumolysin, OMPC, heat shock proteins, pertussis proteins, pneumococcal surface protein PspA or the toxin A or B of *C. difficile*.

Mumps, Measles and Rubella Vaccinal Compositions

Vaccinal compositions comprising mumps, measles and rubella viruses are commonly referred to in the art as "MMR" vaccines. In the practice of the present invention, an MMR vaccine may be achieved by the concomitant administration of a monovalent mumps, monovalent measles and monovalent rubella vaccinal composition. Alternatively, an MMR vaccine may be achieved by a trivalent composition comprising attenuated or inactivated mumps, measles and rubella viruses. Additionally, MMR vaccines have been supplemented with inactivated or attenuated varicella zoster virus (VZV) which are termed MMRV vaccines.

Monovalent and multivalent vaccinal compositions for the prevention of measles, mumps, rubella and/or VZV may be employed in the practice of the present invention alone or in combination. The preparation of vaccinal compositions for the prophylaxis against measles, mumps, rubella and/or VZV are well known to those of skill in the art. Examples of measles strains useful in the preparation of measles vaccinal compositions include the Enders-Edmonston, Edmonston-Zagreb and Schwarz measles strains. A monovalent measles vaccinal composition is also referred to as a "measles vaccine". Examples of mumps virus strains useful on the preparation of vaccinal mumps compositions include the Jeryl Lynn, Urabe AM 9, RIT 4385 and Rubini strains. Examples of rubella virus strain useful in the preparation of vaccinal rubella compositions includes the Wistar RA 27/3 and Wistar RA 27/3M strains. Monovalent mumps, measles and rubella vaccines have been approved for use in human beings and are commercially available. Examples of VZV strains useful in the preparation of vaccinal VZV compositions include the Oka/Merck and Oka strains. An example of a commercial monovalent mumps vaccine useful in the practice of the present invention is the Mumpsvax® vaccine (Merck & Co, Whitehouse Station, N.J., USA). An example of a commercially available monovalent measles vaccine useful in the practice of the present invention is the Attenuvax® vaccine (Merck & Co, Whitehouse Station, N.J., USA). An example of a commercially available monovalent rubella vaccine useful in the practice of the present invention is the Meruvax® II vaccine (Merck & Co, Whitehouse Station, N.J., USA). An examples of a commercially available monovalent attenuated VZV vaccines include the Varivax® and Zostavax® vaccines (Merck & Co, Whitehouse Station, N.J., USA) and Okavax (Sanofi Pasteur SA, Lyon FR).

Alternatively, the mumps, measles and rubella vaccinal compositions may be provided in a trivalent vaccinal composition. Trivalent MMR vaccines may be prepared using a vaccinal strains of mumps, measles and rubella viruses described above. Trivalent MMR compositions for vaccination against mumps, measles and rubella have been approved by regulatory authorities and safe and effective for human use and are commercially available. Examples of commercially available trivalent MMR vaccinal compositions include the M-M-R® II vaccine (commercially available from Merck & Co, Whitehouse Station, N.J. USA), the Triviraten Berna® (also referred to as the Berna-MMR) vaccine (commercially available from Berna Biotech, Basel, Switzerland), the Priorix™ vaccine (commercially available from Glaxo SmithKline Biologics, Rixensart, Belgium), and the Trimovax® vaccine (commercially available Sanofi Pasteur SA, Lyon, France).

Alternatively, measles, mumps, rubella and/or VZV vaccines employed in a tetravalent vaccinal composition. Trivalent MMRV vaccines may be prepared using a vaccinal strains of measles, mumps, rubella and/or VZV described above. Tetravalent MMR compositions for vaccination against measles, mumps, rubella and/or VZV have been approved for human use and are commercially available. Examples of tetravalent MMR vaccinal compositions are commercially available such as ProQuad (Merck and Company, Whitehouse Station N.J. USA) and Priorix Tetra® (commercially available from Glaxo SmithKline Biologics, Rixensart, Belgium Inducing Neutralizing Antibodies In the context of this invention, by "vaccinal composition" is meant a composition comprising an immunoeffective quantity of an antigen sufficient to induce a specific immune response comprising neutralizing antibodies against a pathogen in an immunocompetent mammal. Examples of vaccinal compositions useful in the practice of the present invention are vaccinal dengue compositions, vaccinal dengue viruses, vaccinal dengue immunoproteins, measles vaccines, mumps vaccinal compositions, VZV vaccinal compositions, rubella vaccinal compositions, MMR vaccines and MMRV vaccines individually and collectively. The term is used collectively or individually, as the context provides, where certain procedures or aspects of the invention may be applied to one or more examples of each class of compositions.

The detection of serum neutralizing antibodies to dengue serotypes, mumps, measles rubella and/or VZV are well known in the scientific literature. An example of such a dengue seroneutralization assay is described in Example 1 below. Alternatively, there are commercially available kits for identification of serum neutralizing antibodies against dengue, mumps, measles and rubella. A serum sample is regarded as being positive for the presence of neutralizing antibodies to a vaccinal composition when the titer of neutralizing antibodies so determined is not less than 1:10 (unity: 1/dilution). In alternative embodiments, the serum sample from a mammal to which the dengue vaccinal composition is administered demonstrates the presence of serum neutralizing antibodies to dengue structural proteins at serial dilution factors of 16, 32, 64, 128, 256, 512, 1024, 2048, 4096, or greater.

Mammal

The term mammals includes individuals of the mammalian family, including cows, dogs, horses, primates, human beings, pigs, rabbits, cats. It has been demonstrated that dengue viruses are capable of infecting mammals in addition to human beings including rodents and marsupials. See, e.g. *Dengue infection in neotropical forest mammals*, deThoissy, et al. (2009) Vector Borne Zoonotic Disease 9(2):157-70., A mammal suitable for administration of the compositions and methods of the present invention includes both mammals who have never been exposed to dengue, measles, mumps, rubella and/or VZV virus(es) (i.e. immunologically naïve) or those who have been previously exposed to one or more dengue virus serotypes and/or measles, mumps, rubella and/or VZV including mammals who have exhibited the symptoms of one or more the disease states associated with dengue, mumps, measles, VZV or rubella viral infections (i.e. not naïve). An immunocompetent mammal is a mammal possessing a functional immune system capable of eliciting the production of serum neutralizing antibodies when said mammal is exposed to a vaccinal composition.

Durable

The immune response to a vaccinal composition is said to be "durable" if the serum of mammal, when sampled at future time points following inoculation, maintains the presence serum neutralizing antibodies against the pathogen from which the inoculated vaccinal composition is derived. In the context of the present invention, a durable immune response is demonstrated where a mammal to which a vaccinal composition of the present invention has been administered displays a titer of 1:4, 1:8, 1:16, 1:32 or greater against the antigens administered for a period of 90 days, 120 days, 150 days, 180 days, 210 days, 240 days, 270 days, 300 days, 330 days, one year, two years, 5 years or longer.

Immunization

The term "inoculate" refers to the administration of a vaccinal composition. The term "to immunize" refers to biological response to an inoculation of a vaccinal composition in an immunocompetent mammal resulting in the durable presence of neutralizing antibodies against a pathogen from which said antigen was derived. The response to inoculation with single vaccinal composition may result in the production of serum neutralizing antibodies against a single pathogen, variants of said pathogen or different pathogens which is termed cross-reactivity. Vaccinal compositions of the present invention may demonstrate cross-reactivity so as to immunize an immunocompetent mammal against multiple pathogens or different variants of the same pathogen. A mammal is said to be "immunized" with respect to a particular pathogen if that mammal durably maintains serum neutralizing antibodies against pathogen and retains an inducible immunologic memory permitting said mammal to produce sufficient neutralizing antibodies against said pathogen to minimize or avoid the symptoms of disease states associated with said pathogen in said mammal upon rechallenge with said pathogen.

Vaccinal Dengue Virus Dose

The quantities of vaccinal virus compositions included in a unit dosage form are commonly expressed in terms of viral plaque forming units (PFU) or doses infecting 50% of the tissue culture or again doses infecting 50% of the cell culture ($CCID_{50}$). For example, compositions according to the invention may contain 10 to $10^6$ $CCID_{50}$, in particular $10^3$ to $10^5$ $CCID_{50}$ of vaccinal dengue virus of serotypes 1, 2, 3 or 4 for a monovalent or tetravalent composition. Thus, in the compositions or utilizations according to the invention the doses of vaccinal dengue viruses of serotypes 1, 2, 3 and 4 preferably each lie within a range from 10 to $10^6$ $CCID_{50}$, such as 10, $10^2$, $10^3$, $10^4$, $10^5$ or $10^6$ $CCID_{50}$, in particular within a range from $10^3$ to $10^5$ $CCID_{50}$. A vaccinal virus may be used at the same or different doses, which can be adjusted in relation to the nature of the vaccinal virus used and the intensity of the immune response obtained.

Alternatively, the vaccinal virus compositions included in a unit dosage form may be described by the quantity or concentration of virus particles in a given preparation. The quantity or concentration of viral particles may be determined using conventional spectrophotometric or immunoassay protocols. Using a given assay method of determining PFU, the skilled artisan may readily establish a standard curve for such assay to readily convert a PFU dosage to a dosage form based on quantity or concentration of viral particles.

According to a particular embodiment of a method according to this invention, the quantities of attenuated vaccinal dengue virus in monovalent and tetravalent compositions or vaccines are $10^3$ to $10^5$ $CCID_{50}$. According to a particular embodiment, the monovalent vaccine comprises $10^4$ $CCID_{50}$ of VDV1 or VDV2, preferably VDV2. According to a particular embodiment, the tetravalent vaccine comprises $10^5$ $CCID_{50}$ of CHIMERIVAX™ DEN-1, 2, 3 and 4 (CYD DEN-1,2,3,4). According to one advantageous embodiment, the tetravalent vaccine comprises $10^5$ $CCID_{50}$ of CHIMERIVAX™ (CYD) DEN-1, 2 and 3 and $10^3$ $CCID_{50}$ of CHIMERIVAX™ (CYD) DEN-4. In another embodiment of the invention, the tetravalent dengue vaccinal composition comprising attenuated $5 \pm 1$ $\log_{10}$ $CCID_{50}$ CHIMERIVAX™ (CYD) viruses encoding the prM and E genes of dengue serotypes 1, 2, 3, and 4 is administered in a unit dosage volume of 0.5 ml.

Formulation of the Unit Dosage Form

The vaccinal compositions of the present invention may also include one or more pharmaceutically acceptable vehicles. The term "vehicle" refers to compounds commonly used on the formulation of pharmaceuticals and vaccines to enhance stability, sterility and deliverability of the active agent. Suitable vehicles and their preparation are described, for example, in Remington's Pharmaceutical Sciences, $16^{th}$ Edition, A. Osol, Ed., Mack Publishing Co., Easton, Pa. (1980), and Remington's Pharmaceutical Sciences, $19^{th}$ Edition, A. R. Gennaro, Ed., Mack Publishing Co., Easton, Pa. (1995).

When the vaccinal composition is formulated as a solution or suspension, the immunologically active agent is provided in a pharmaceutically acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques including sterile filtration via a 0.2 micron pore filter. The resulting aqueous solutions may be packaged for use. Alternatively, the aqueous solutions may be lyophilized, the lyophilized preparation being reconstituted with a sterile aqueous solution prior to administration.

The vaccinal compositions may optionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorption monolaurate, triethanolamine oleate, human serum albumin, essential amino acids, non-essential amino acids, L-arginine hydrochlorate, saccharose, D-trehalose dehydrate, sorbitol, tris (hydroxymethyl) aminomethane and/or urea.

In addition, the vaccinal composition may optionally comprise pharmaceutically acceptable additives including, for example, diluents, binders, stabilizers, and preservatives.

Unit dosage formulations of the vaccinal compositions of the present invention may be included in a kit of products containing the vaccinal virus in lyophilized form and a solution for reconstitution of the lyophilized product. Recombinant viruses of the present invention may be lyophilized by conventional procedures and reconstituted. Such solutions for reconstitution of the lyophilized vaccinal composition may be aqueous solvents comprising buffers, organic or inorganic salts, and agents to assist in solubilization.

Adjuvants

The vaccinal composition may optionally comprise one or more adjuvants to enhance the immunogenicity of the vaccinal composition in a mammal. Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes.

Alternatively, the adjuvant may be an oil-in-water emulsion adjuvants (EP 0 399 843B), as well as combinations of oil in water emulsions and other active agents (WO 95/17210; WO 98/56414; WO 99/12565; WO 99/11241). Other oil emulsion adjuvants have been described, such as water-in-oil emulsions (U.S. Pat. No. 5,422,109; EP 0 480 982 B2) and water-in-oil-in-water emulsions (U.S. Pat. No. 5,424,067; EP 0 480 981 B). Examples of such adjuvants include MF59, AF03, AF04, AF05, AF06 and derivatives thereof.

Alternatively, the adjuvant may be a saponin, lipid A or a derivative thereof, an immunostimulatory oligonucleotide, an alkyl glucosamide phosphate, an oil in water emulsion or combinations thereof. Examples of saponins include Quil A and purified fragments thereof such as QS7 and QS21.

Routes of Administration

The administration or co-administration of the vaccinal compositions of the present invention may be achieved by transcutaneous, subcutaneous, intramuscular or intradermal injection. The vaccinal compositions may be administered using conventional hypodermic syringes or safety syringes such as those commercially available from Becton Dickinson Corporation (Franklin Lakes, N.J., USA) or jet injectors. For intradermal administration, conventional hypodermic syringes may be employed using the Mantoux technique or specialized intradermal delivery devices such as the BD Soluvia™ microinjection system (Becton Dickinson Corporation, Franklin Lakes, N.J., USA). may also be employed.

Dosage Regimens

In one embodiment of the invention, the vaccinal dengue composition comprising four serotypes of dengue is co-administered with an MMR vaccine to an immunocompetent mammal. In one embodiment of the invention, the vaccinal dengue composition comprising four serotypes of dengue is co-administered with a monovalent measles vaccine to an immunocompetent mammal. In one embodiment of the invention, the vaccinal dengue composition comprising four serotypes of dengue is co-administered with an MMRV vaccine to an immunocompetent mammal. By the term co-administration, it is meant that the compositions are administered to an individual within 3 days, 2 days, 24 hours, 12 hours, 6 hours, 3 hours, 2 hours, 1 hour, 30 minutes, 15 minutes or simultaneously. In one embodiment, the immunocompetent mammal is a human being less than 48, 36 or 24 months of age.

In one embodiment, the invention provides a multi-step dosage regimen. An initial co-administration of the dengue vaccinal composition and either the monovalent measles, MMR or MMRV vaccinal compositions is performed at a time $T_0$ and may be enhanced by the administration of a second administration of vaccinal dengue composition of four serotypes of dengue at a date approximately 1, 2, 3, 4, 5, 6, 7, 8, or 9 months following $T_0$. In one embodiment, this initial co-administration event may be supplemented by the administration of a second administration of vaccinal dengue composition of four serotypes of dengue at a date approximately 1, 2, 3, 4, 5, 6, 7, 8, or 9 months following $T_0$ (this second administration being administered on a date termed $T_1$) and a third administration of vaccinal dengue composition of four serotypes of dengue at a date approximately 1, 2, 3, 4, 5, 6, 7, 8, or 9 months following T1 (this third administration being administered on a date termed $T_2$).

In another embodiment, the invention provides a dosage regimen wherein at an intermediate time point between, $T_1$ and $T_2$, the mammal is administered a vaccinal composition comprising the diphtheria, tetanus, pertussis, poliomyelitis and Hib antigens (referred to herein as a "combo") vaccine. The combo vaccine is administered at a date approximately 1, 2, 3, 4, 5 or 6 months following $T_1$ and then subsequently followed administration of a tetravalent vaccinal dengue composition at $T_2$.

In one embodiment of the invention as exemplified herein, a human being is immunized against the four serotypes of dengue, mumps, measles and rubella in accordance with the following procedure:

(1) At time $T_0$, a human being is injected subcutaneously in one arm with a quantity of $10^{5\pm1}$ CCID$_{50}$ for each CYD DEN 12,3,4 serotype for the tetravalent vaccine in a volume of 0.5 ml and subcutaneously in the other arm with an MMR vaccine. Both injections are performed within a period of 3 hours. In one embodiment, the human being is less than 36 months of age at the time $T_0$. In one embodiment, the MMR vaccine is Trimovax® (Sanofi Pasteur Lyon FR).

(2) Approximately six months after $T_0$ (time $T_1$), the same human being who received the initial immunization described above, receives a second subcutaneous administration of a tetravalent vaccinal dengue compositions comprising a quantity of $10^{5\pm1}$ CCID$_{50}$ for each CYD DEN 1,2,3,4 serotype in a volume of 0.5 ml. No MMR vaccine is required to be administered at this time.

(3) Approximately six months after $T_1$ (time $T_2$), the same human being who received the initial immunization described above, receives a second subcutaneous administration of a tetravalent vaccinal dengue compositions comprising a quantity of $10^{5\pm1}$ CCID$_{50}$ for each CYD DEN 12,3,4 serotype in a volume of 0.5 ml. No MMR vaccine is required to be administered at this time.

The invention also provides an alternative immunization schedule in substantial accordance with the foregoing three-step schedule which adds an additional immunization with a "combo" vaccine at an intermediate time point between $T_1$ and $T_2$. Preferably, at a time point approximately 3 three months following $T_1$ (administration of the second dose of the DEN-1,2,3,4 composition) the same human being is given an intramuscular injection of a "combo" vaccine. In one embodiment the combo vaccine is which is a pharmaceutical formulation containing, in addition to excipients and aluminum hydroxide adjuvant, at least 30 IU diphtheria toxoid, at least 40 IU tetanus toxoid, approximately 25 micrograms of *Bordatella pertussis* toxoid and filamentous hemagglutinin antigens, approximately 40 DU of inactivated Type 1 poliomyelitis virus, approximately 40 DU of inactivated Type 1 poliomyelitis virus, approximately 8 DU of inactivated Type 2 poliomyelitis virus, approximately 32 DU of inactivated Type 3 poliomyelitis virus, and approximately 10 micrograms of the polysaccharide of *Haemophilus influenzae* type b conjugated to tetanus toxin in a volume of 0.5 ml. The combo vaccine may be Pentaxim® (Sanofi Pasteur, Lyon FR). At a time point approximately three months following the administration of the combo vaccine ($T_2$), the same human being receives a third subcutaneous administration of a tetravalent vaccinal dengue compositions comprising a quantity of $10^{5\pm1}$ CCID$_{50}$ for each CYD DEN 1 to 4 serotype in a volume of 0.5 ml. No MMR vaccine is required to be administered at this time.

Blood samples are taken from the human being at selected time points during the foregoing dosing regimen and at defined time points thereafter. The serum from such samples is isolated and evaluated for the presence of neutralizing antibodies to the antigens administered in the dosage regimen in accordance with the teaching of the specification and techniques well known in the art.

Booster administrations of the vaccinal dengue compositions, MMR vaccines and/or "combo" vaccines may be administered subsequent to the foregoing dosage regimen to maintain robust immunoprotection in the mammal. Such booster administrations may occur at time points of approximately 1 year, 2 years, 3 years, 4 years, 5 years, 10 years, or longer.

Immunization Kit

According to another aspect, this invention has as its object a kit to achieve against the four serotypes of dengue fever virus, mumps, measles and rubella. The kit according to this invention comprises vaccinal compositions as described in relation to the method of immunization proposed. The kit according to the invention therefore comprises a box containing various containers holding the compositions or vaccines and advantageously an explanatory brochure including useful information for administration of the said compositions or vaccines. The term container includes conventional sealed vials and prefilled syringes.

According to one embodiment, this invention therefore relates to a kit for immunization against dengue serotypes 1, 2, 3, and 4, as well as either (1) measles, or (2) measles, mumps and rubella or (3) measles, mumps, rubella and VZV, comprising a box containing at least (a) a first container holding either a monovalent measles, trivalent MMR, or tetravalent MMRV vaccine, respectively, and (b) a second container holding a tetravalent dengue vaccine.

The vaccinal compositions which may be used in the kit according to the invention include the vaccinal compositions described herein in relation to the method of immunization according to the invention.

If the vaccinal compositions are provided in lyophilized form, the kit will advantageously comprise at least one additional container holding a solution which can be used to reconstitute a lyophilized vaccinal composition suitable for administration by intradermal, transcutaneous, subcutaneous, or intramuscular administration. Pharmaceutically acceptable diluents and carriers may be used for reconstitution.

According to a particular embodiment, the kit according to the invention comprises a tetravalent vaccine comprising $10^{5\pm1}$ $CCID_{50}$ of CHIMERIVAX™ (CYD) DEN-1, 2, 3 and 4.

The container in which the pharmaceutical formulation is packaged prior to use can comprise a hermetically sealed container enclosing an amount of the lyophilized formulation or a solution containing the formulation suitable for a pharmaceutically effective dose thereof, or multiples of an effective dose. The pharmaceutical formulation is packaged in a sterile container, and the hermetically sealed container is designed to preserve sterility of the pharmaceutical formulation until use.

Optionally, the container can be associated with administration means and or instruction for use. Examples of administration means may include syringes for parenteral administration or delivery systems to facilitate intradermal administration.

Pharmaceutical Dosage Forms

The volume of vaccinal composition administered will depend on the method of administration. In the case of subcutaneous injections, the volume is generally between 0.1 and 1.0 ml, preferably approximately 0.5 ml.

The optimum period for administering all serotypes 1 to 4 is approximately 1 to 3 months before potential exposure to dengue fever virus. The compositions of the present invention may be administered as a prophylactic treatment against infection by dengue fever virus in adults and children. Target populations therefore include persons who may be naïve (i.e. not previously immunized) or non-naïve with regard to dengue fever virus.

Booster administrations of dengue fever vaccinal viruses of serotypes 1 to 4 may also be used for example between 6 months and 10 years, for example 6 months, 1 year, 3 years, 5 years or 10 years after administration of the last immunization.

EXAMPLES

The following Examples are illustrative of the practice of the present invention and not intended to be limiting on the scope of the practice of the present invention as provided above.

Example 1: Collection and Preservation of Serum Samples

Experiments on monkeys are carried out in accordance with European Directives relating to animal experiments. The immunizations are performed on cynomolgus monkeys (*Macaca fascicularis*) originating from Mauritania. The monkeys are placed in quarantine for six weeks prior to immunization. The monkeys are immunized subcutaneously with 0.5 ml of vaccine composition in the arm.

After mild anesthesia with ketamine (Imalgene, Merial), blood is collected by puncture of the inguinal or saphenal veins. On days 0 and 28 following each immunization, 5 ml of blood are sampled in order to evaluate antibody responses. The blood is collected on ice and preserved on ice until the serum is isolated by centrifugation for 20 minutes at 4° C. The serum is stored at −80° C. until the time of the tests.

Example 2: Measurement of Dengue Neutralizing Antibodies

In a 96 well plate, 0.120 ml of each decomplemented serum isolated in substantial accordance with Example 1 is added to 0.480 ml of diluent (ISCOVE 4% SVF) in each well. Serial dilutions of a factor 6 are performed by transferring 0.150 ml of serum into 0.450 ml of diluent. 450 µl of viral dilution containing 2.7 $\log_{10}$ CCID50/ml are added to each well so as to obtain 25 CCID50/well. The plate is incubated at 37° C. for 1 hour. 0.1 ml of each dilution is then distributed into 6 wells of a 96 well plate in which VERO cells have been seeded 3 days before the start of the experiment at a density of 8000 cells/well in 0.1 ml of ISCOVE 4% SVF medium. After 6 days incubation at 37° C. in the presence of 5% $CO_2$, the cells are fixed using an ethanol/acetone (70/30) mixture at 4° C. for 15 minutes, and then washed 3 times in PBS and incubated for 1 hour at 37° C. in the presence of 0.05 ml of a 1/2000 dilution of an anti-flavivirus monoclonal antibody (mAb 4G2 obtained from an ATCC H-B112 hybridoma). The plates are then washed twice and incubated for 1 hour at 37° C. in the presence of 0.05 ml of a 1/1000 dilution of an anti-mouse IgG conjugated with 2 5 alkaline phosphatase. The lysis plaques are revealed by adding 0.05 ml of a stained substrate: BCIP/NBT. The neutralizing antibody titers are calculated using the Karber formula as defined below:

$$Log_{10} SN50 = d + f/N(X+N/2),$$

in which:
  d: represents the dilution providing 100% neutralization (that is 6 negative replicates, i.e. presenting no signs of infection)
  f: represents the dilution factor as $log_{10}$ (e.g. dilution factor of 1:4, f=0.6)
  N: represents the number of replicates/dilution (N=6)
  X: total number of wells having no sign of infection, with the exception of dilution d.
  The limit for viral detection is 10 SN50 (i.e. 1.0 $log_{10}$ SN50). The viral strains used for neutralization are the strains DEN1 16007, DEN2 16681, DEN3 16562 or DEN4 1036. In the case of the controls, the initial viral dilutions are re-titrated. The correlation between the neutralizing titer measured in the SN50 test and the neutralizing titer measured conventionally in the PRNT50 test is: $log_{10}$ PRNT50=$log_{10}$SN50+0.2.

Example 3. Determination of Measles, Mumps and Rubella Antibodies

Antibody levels against measles, rubella and mumps are measure by ELISA in serum collected 28 days post MMR vaccination. Briefly 96 well plates pre-adsorbed with antigen are exposed to the serum. IgG antibodies in the test sample bind to the pre-adsorbed antigen. Anti-human IgG conjugate binds to the antigen antibody complex. Excess conjugate is removed and a colorimetric substrate added. The enzyme component of the conjugate catalyzes a hydrolytic reaction which converts the substrate and produces a color change. The reaction is quenched at a defined time point. The intensity of the color is proportional to the activity of the virus specific IgG antibodies in the sample. The activity of the virus specific IgG antibodies contained in the sample are quantified by a standard curve generated using the reference standard (obtainable from the World Health Organization) and a four parameter logistic regression function. Results are reported in mIU/mL and the lower limit of quantitation of this assay is 120 mIU/mL.

Example 4. Production of CHIMERIVAX™ (CYD)

Each monovalent CHIMERIVAX™ (CYD) dengue fever vaccinal virus (serotypes 1, 2, 3 and 4) is prepared by amplifying each serotype in Vero cells. More specifically, the four viruses are produced separately in adherent Vero cells in a serum-free medium. The viral harvest, clarified from cell debris by filtration, is then concentrated and purified by ultrafiltration and chromatography to remove the DNA from the host cells. After adding a stabilizing agent, the vaccinal strains are stored in a frozen or lyophilized form before use and then reconstituted as needed. The same process is applied to the four chimeras.

Example 5. Dengue MMR Serum Immunization

Immunization against measles, mumps, rubella and the four serotypes of dengue virus is achieved in substantial accordance with the following procedure. An initial inoculation with a tetravalent dengue vaccinal compositions is performed subcutaneously in the arm using a 23G1 needle, with a quantity of $10^{5\pm1}$ $CCID_{50}$ for each CYD DEN 1 to 4 serotype for the tetravalent vaccine in a volume of 0.5 ml and an inoculation with an MMR vaccine containing at least 1000 $CCID_{50}$ measles virus (Schwarz strain) at least 5000 $CCID_{50}$ mumps virus (Urabe AM-9 strain) and at least 1000 $CCID_{50}$ rubella virus (Wistar RA 27/3M) in a volume of 0.5 ml. Administration of the tetravalent dengue vaccinal composition and MMR vaccines is achieved by the subcutaneous administration of a 0.5 ml sample of each vaccinal composition into each arm of a human being less than 24 months of age within 1 hour. The MMR vaccine may be Trimovax® (Sanofi Pasteur Lyon FR).

The same human being who is inoculated with the co-administered compositions described above, is inoculated a second time by subcutaneous administration of a tetravalent vaccinal dengue composition comprising a quantity of $10^{5\pm1}$ $CCID_{50}$ for each CYD DEN 1 to 4 serotype in a volume of 0.5 ml approximately six months following the first administration. No MMR vaccine is administered at this time.

At a time approximately six months following the second subcutaneous administration of a tetravalent vaccinal dengue composition described immediately above, the same human being is inoculated a third time by subcutaneous administration of a tetravalent vaccinal dengue compositions comprising a quantity of $10^{5\pm1}$ $CCID_{50}$ for each CYD DEN 1 to 4 serotype in a volume of 0.5 ml.

Blood samples are taken from the human being at selected time points during the foregoing dosing regimen and at defined time points thereafter. The serum from such samples is isolated and evaluated for the presence of neutralizing antibodies to the antigens administered in accordance with the teaching of the specification and techniques well known in the art. The data demonstrate immunization against measles, mumps, rubella viruses and four serotypes of dengue virus.

Example 6. Dengue MMR Combo Immunization

Immunization against measles, mumps, rubella, the four serotypes of dengue virus as well as diphtheria, tetanus, pertussis, poliomyelitis and Hib antigens is achieved in substantial accordance with the following procedure. An initial co-administration is performed subcutaneously in the arm using a 23G1 needle, inoculating the subject with a quantity of $10^{5\pm1}$ $CCID_{50}$ for each CYD DEN 1 to 4 serotype for the tetravalent vaccine in a volume of 0.5 ml and inoculation of the subject with the MMR vaccine Trimovax® (Sanofi Pasteur) containing at least 1000 $CCID_{50}$ measles virus (Schwarz strain) at least 5000 $CCID_{50}$ mumps virus (Urabe AM-9 strain) and at least 1000 $CCID_{50}$ rubella virus (Wistar RA 27/3M) in a volume of 0.5 ml. Administration of the tetravalent dengue vaccine and MMR vaccines is achieved by the subcutaneous administration of a 0.5 ml sample of each vaccine into each arm of a human being less than 24 months of age within 1 hour.

The same human being who receives the initial co-administration of tetravalent vaccinal dengue compositions and MMR vaccine described above, receives a second inoculation of a dengue vaccinal composition by subcutaneous administration of a tetravalent vaccinal dengue composition comprising a quantity of $10^{5\pm1}$ $CCID_{50}$ for each CYD DEN 1 to 4 serotype in a volume of 0.5 ml approximately six months following the first administration. No MMR vaccine is administered at this time.

Approximately 3 months following the second tetravalent dengue vaccinal administration, the same human being is inoculated by intramuscular injection of a "combo" vaccine which is a pharmaceutical formulation containing, in addition to excipients and aluminum hydroxide adjuvant, at least 30 IU diphtheria toxoid, at least 40 IU tetanus toxoid, approximately 25 micrograms of *Bordatella pertussis* toxoid and filamentous hemagglutinin antigens, approximately 40 DU of inactivated Type 1 poliomyelitis virus, approximately 40 DU of inactivated Type 1 poliomyelitis virus, approximately 8 DU of inactivated Type 2 poliomyelitis virus, approximately 32 DU of inactivated Type 3 poliomyelitis virus, and approximately 10 micrograms of the polysaccharide of *Haemophilus influenzae* type b conjugated to tetanus toxin in a volume of 0.5 ml. The combo vaccine may be Pentaxim® (Sanofi Pasteur, Lyon FR).

At a time approximately three months following the administration of the combo vaccine, the same human being receives a third subcutaneous administration of a tetravalent vaccinal dengue composition comprising a quantity of $10^{5\pm1}$ $CCID_{50}$ for each CYD DEN 1 to 4 serotype in a volume of 0.5 ml.

Blood samples are taken from the human being at selected time points during the foregoing dosing regimen and at defined time points thereafter. The serum from such samples is isolated and evaluated for the presence of neutralizing antibodies to the antigens administered in accordance with the teaching of the specification and techniques well known in the art. The data demonstrate immunization against measles, mumps, rubella viruses, diphtheria, pertussis, Hib, tetanus and four serotypes of dengue virus.

Example 7. Measles and Dengue Immunization

Immunization against measles and the four serotypes of dengue virus is achieved in substantial accordance with the teaching of Example 5 hereinabove, except that the MMR vaccine is replaced with a monovalent measles vaccine.

Example 8. Measles, Dengue and Combo Immunization

Immunization against measles, the four serotypes of dengue virus as well as diphtheria, tetanus, pertussis, poliomyelitis and Hib antigens is achieved in substantial accordance with the teaching of Example 6 hereinabove, except that the MMR vaccine is replaced with a monovalent measles vaccine.

Example 9. MMRV and Dengue Immunization

Immunization against measles, mumps, rubella, and VZV and the four serotypes of dengue virus is achieved in substantial accordance with the teaching of Example 5 hereinabove, except that the MMR vaccine is replaced with a tetravalent MMRV vaccine.

Example 10 MMRV, Dengue and Combo Immunization

Immunization against measles, mumps, rubella, and VZV, the four serotypes of dengue virus as well as diphtheria, tetanus, pertussis, poliomyelitis and Hib antigens is achieved in substantial accordance with the teaching of Example 6 hereinabove, except that the MMR vaccine is replaced with a MMRV measles vaccine.

The invention claimed is:

1. A method of inducing neutralizing antibodies against serotypes 1, 2, 3, and 4 of dengue virus, mumps virus, measles virus, and rubella virus in a mammal, comprising the administration of a tetravalent immunogenic composition comprising live attenuated dengue viruses of serotypes 1, 2, 3, and 4 and the co-administration of a trivalent live attenuated MMR vaccinal composition to said mammal, wherein the tetravalent immunogenic composition and the trivalent live attenuated MMR vaccinal composition are administered to said mammal within 24 hours of each other, there is compatibility between the different antigens, and each individual antigen is able to induce an immunological response.

2. The method of claim 1 wherein the tetravalent immunogenic composition comprises (i) a chimeric flavivirus comprising the genome of a yellow fever virus in which sequences coding for pre-membrane (prM) and envelope (E) proteins have been replaced with sequences encoding prM and E of dengue virus serotype 1, (ii) a chimeric flavivirus comprising the genome of a yellow fever virus in which sequences coding for prM and E proteins have been replaced with sequences encoding prM and E of dengue virus serotype 2, (iii) a chimeric flavivirus comprising the genome of a yellow fever virus in which sequences coding for prM and E proteins have been replaced with sequences encoding prM and E of dengue virus serotype 3, and (iv) a chimeric flavivirus comprising the genome of a yellow fever virus in which sequences coding for prM and E proteins have been replaced with sequences encoding prM and E of dengue virus serotype 4.

3. The method of claim 1 wherein the quantity of live attenuated dengue viruses of serotypes 1, 2, 3, and 4 lies within a range from $10^3$ to $10^6$ $CCID_{50}$.

4. A kit against dengue fever, mumps, measles, and rubella comprising a box containing at least (a) a first container holding a trivalent live attenuated MMR vaccine, and (b) a second container holding a tetravalent immunogenic composition comprising live attenuated dengue viruses of serotypes 1, 2, 3, and 4.

5. The kit of claim 4 further comprising a third container holding a solvent for reconstitution.

6. The kit of claim 4 or 5 wherein the container is a pre-filled syringe.

7. The method of claim 1, wherein the tetravalent immunogenic composition comprising live attenuated dengue viruses of serotypes 1, 2, 3, and 4 and the trivalent live attenuated MMR vaccinal composition are administered to said mammal within 1 hour of each other.

* * * * *